(12) United States Patent
Bassler et al.

(10) Patent No.: US 6,479,680 B1
(45) Date of Patent: Nov. 12, 2002

(54) METHOD FOR REACTING AN ORGANIC COMPOUND WITH A HYDROPEROXIDE

(75) Inventors: Peter Bassler, Viernheim; Wolfgang Harder, Weinheim; Peter Resch, Hettenleidelheim; Norbert Rieber, Mannheim; Wilhelm Ruppel, Frankenthal; Joaquim Henrique Teles, Altrip; Andreas Walch, Schwaigern; Anne Wenzel, Graben-Neudorf; Peter Zehner, Lugwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/762,290

(22) PCT Filed: Aug. 9, 1999

(86) PCT No.: PCT/EP99/05740

§ 371 (c)(1),
(2), (4) Date: Feb. 7, 2001

(87) PCT Pub. No.: WO00/07965

PCT Pub. Date: Feb. 17, 2000

(30) Foreign Application Priority Data

Aug. 7, 1998 (DE) .......................................... 198 35 907

(51) Int. Cl.$^7$ ............................................. C07D 301/12
(52) U.S. Cl. ....................... 549/529; 549/531; 210/294; 210/322
(58) Field of Search ................................. 549/529, 531; 210/294, 322

(56) References Cited

U.S. PATENT DOCUMENTS

| | | | |
|---|---|---|---|
| 4,833,260 A | 5/1989 | Nerl et al. | 549/531 |
| 4,977,285 A | 12/1990 | Marquis et al. | 549/529 |
| 5,262,550 A | 11/1993 | Crocco et al. | 549/531 |
| 5,274,138 A | 12/1993 | Keating et al. | 549/529 |
| 5,349,072 A | 9/1994 | Preston et al. | 549/529 |
| 5,374,747 A | 12/1994 | Saxton et al. | 549/531 |
| 5,384,418 A | 1/1995 | Zajacek et al. | 549/531 |
| 5,463,090 A | 10/1995 | Rodriguez et al. | 549/531 |

FOREIGN PATENT DOCUMENTS

| | | |
|---|---|---|
| EP | 0 031 537 | 7/1981 |
| EP | 0 568 336 | 11/1993 |
| EP | 0 659 473 | 6/1995 |

OTHER PUBLICATIONS

Hydrocarbon Processing, pp. 112 and 126, "Refining Handbook", Nov. 1990.

*Primary Examiner*—Ba K. Trinh
(74) *Attorney, Agent, or Firm*—Oblon, Spivak, McClelland, Maier & Neustadt, P.C.

(57) ABSTRACT

A process for the reaction of an organic compound with a hydroperoxide comprises at least the steps (i) to (iii) below:

Figure 1:
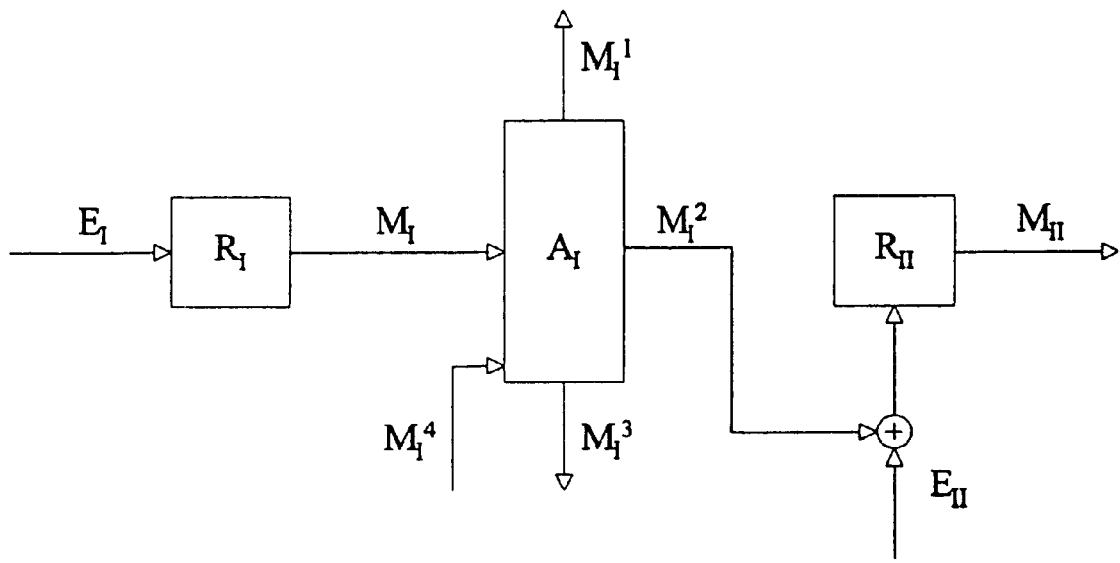

(i) reaction of the hydroperoxide with the organic compound to give a mixture comprising the reacted organic compound and unreacted hydroperoxide, (ii) separation of the unreacted hydroperoxide from the mixture resulting from step (i), (iii) reaction of the hydroperoxide separated off in step (ii) with the organic compound.

15 Claims, 1 Drawing Sheet

METHOD FOR REACTING AN ORGANIC COMPOUND WITH A HYDROPEROXIDE

This application is a 371 of PCT/EP 99/05740 dated Aug. 9, 1999.

The present invention relates to a process for the reaction of an organic compound with a hydroperoxide, during the course of which hydroperoxide is separated off and reacted again with the organic compound. The present invention likewise relates to an apparatus for the reaction of an organic compound with a hydroperoxide.

Reactions of organic compounds with hydroperoxides, i.e. with compounds of the formula ROOH, are generally carried out in one step in customary processes of the prior art.

In this context, the term "in one step" relates to the hydroperoxide starting material and means that hydroperoxide is added to the respective organic compound only in a single step during the overall process.

For example, U.S. Pat. No. 5,262,550 describes a process for the epoxidation of alkenes, in which alkene is reacted with hydrogen peroxide or a hydrogen peroxide precursor in one step to give the corresponding alkene oxide.

U.S. Pat. No. 4,883,260 discloses a process in which alkene is reacted with hydrogen peroxide in one step in a steel autoclave or in a glass autoclave.

S.-H. Wang, Process Economics Program, Report 2E, pp. 6-1 to 6-27, SRI International (1994), describes, for example, a process in which an about 17% strength by weight ethylbenzene hydroperoxide solution is reacted with propene in one step over a homogeneous Mo catalyst. A total of 7.2 mol of propene are used per mole of hydroperoxide in this process.

The same document discloses, on pages 6-28 to 6-47, a process in which an about 20% strength by weight ethylbenzene hydroperoxide solution is reacted with propene in one step over a heterogeneous $TiO/SiO_2$ catalyst, with the alkene being epoxidized. Here, 16.7 mol of propene are used per mole of hydroperoxide.

This document likewise discloses, on pages 5-1 to 5-21, a process in which an about 40% strength by weight tert-butyl hydroperoxide solution is reacted with propene in one step over a homogeneous Mo catalyst, with the alkene being epoxidized. Here, 3.7 mol of propene are used per mole of hydroperoxide.

The same document discloses, on pages 5-22 to 5-43, a process in which an about 72% strength by weight tert-butyl hydroperoxide solution is reacted with propene over a homogeneous Mo catalyst in two directly successive steps, with the alkene being epoxidized. Here, 1.2 mol of propene are used per mole of hydroperoxide.

A disadvantage of these processes is that it is necessary either to employ a relatively high excess of the organic compound to be reacted or to employ a very concentrated hydroperoxide in order to achieve optimal selectivity.

It is an object of the present invention to provide a process which allows the excess of organic compound to be reacted to be kept as low as possible and a relatively low-concentration hydroperoxide to be used.

We have found that this object is achieved by a process for the reaction of an organic compound with a hydroperoxide, which comprises at least the steps (i) to (iii) below:

(i) reaction of the hydroperoxide with the organic compound to give a mixture comprising the reacted organic compound and unreacted hydroperoxide, (ii) separation of the unreacted hydroperoxide from the mixture resulting from step (i), (iii) reaction of the hydroperoxide separated off in step (ii) with the organic compound.

Accordingly, the reaction of the organic compound with the hydroperoxide takes place in at least two steps (i) and (iii). In the process of the present invention, it is likewise conceivable for the reaction of the organic compound with the hydroperoxide to take place in more than two steps. Depending on the number of steps in which the reaction takes place, it is of course also conceivable for more than one step in which the hydrogen peroxide used is separated off to be employed in the process of the present invention.

An example which may be mentioned is a process in which the reaction of the organic compound with the hydroperoxide takes place in steps (i), (iii) and (v), and the separation of the hydroperoxide takes place in steps (ii) and (iv).

In general, from two to five steps in which the organic compound is reacted with the hydroperoxide are employed in the process of the present invention. The present invention therefore also provides a process for the reaction of an organic compound with a hydroperoxide, which comprises the steps (i) to (ix) below:

(i) reaction of the hydroperoxide with the organic compound to give a mixture $M_I$, (ii) separation of the hydroperoxide from the mixture $M_I$ resulting from step (i), (iii) reaction of the hydroperoxide separated off in step (ii) with the organic compound to give a mixture $M_{II}$, (iv) separation of the hydroperoxide from the mixture $M_{II}$ resulting from step (iii), (v) reaction of the hydroperoxide separated off in step (iv) with the organic compound to give a mixture $M_{III}$, (vi) separation of the hydroperoxide from the mixture $M_{III}$ resulting from step (v), (vii) reaction of the hydroperoxide separated off in step (vi) with the organic compound to give a mixture $M_{IV}$, (viii) separation of the hydroperoxide from the mixture $M_{IV}$ resulting from step (vii), (ix) reaction of the hydroperoxide separated off in step (viii) with the organic compound.

The process of the present invention preferably has from two to four steps in which the organic compound is reacted with hydroperoxide, particularly preferably from two to three steps. The reaction of the organic compound with the hydroperoxide preferably takes place in two steps.

The separation of the hydroperoxide in the abovementioned separation steps (ii), (iv), (vi) and (viii) in the process of the present invention can be carried out by all customary methods of the prior art. It is also possible to use different separation methods in different separation steps.

The separation of the hydroperoxide in the separation steps is preferably carried out by distillation. Depending on the requirements of the process, separation in one or more distillation columns is possible. Preference is given to using one distillation columns for separating off the hydroperoxide in one separation step.

In the process of the present invention, it is conceivable for a dedicated separation apparatus $A_i$ to be provided for each step in which the hydroperoxide is separated off. It is likewise possible, in the case of an appropriate reaction procedure and a plurality of separation steps, for the separations to be carried out in a single separation apparatus.

If a plurality of separation steps are provided, it is also possible, by means of a suitable reaction procedure, to carry out two or more separation steps in one separation apparatus. Accordingly, it is quite generally possible for a total of m separation apparatuses to be provided for n separation steps, where $1 \leq m \leq n$.

Should a further separation of the hydroperoxide be desired subsequent to the last stage in which reaction of the organic compound with the hydroperoxide takes place, for example to recycle any residual hydroperoxide, this is of course likewise possible within the scope of the process of the present invention.

In the process of the present invention, not only the hydroperoxide but also the reacted organic compound can be separated off in a separation apparatus from the mixture resulting from a reaction step in which the organic compound is reacted with the hydroperoxide. It is naturally also possible for the remaining reaction product after the hydroperoxide has been separated off to be transferred to a further separation apparatus provided specifically for this purpose and the reacted organic compound to be separated from the reaction product there.

In both cases, it is possible, for example, to collect the reacted organic compound in the m separation apparatuses and to separate it off after the reactions of the organic compound with the hydroperoxide are complete.

However, the reacted organic compound is preferably separated off in addition to the hydroperoxide in the respective separation apparatus. In the case of separation by distillation, it is possible, for example, to take off the reacted organic compound from the mixture at the top and to separate the hydroperoxide from the mixture at a side offtake.

In the process of the present invention, it is naturally likewise possible, when using a distillation unit as separation apparatus, to separate the hydroperoxide from the mixture not at a side offtake but at the bottom.

If the hydroperoxide and/or the reacted organic compound are/is separated off in a distillation unit, it is possible, in the process of the present invention, for any high-boiling components of the mixture, which are formed as by-products in the reaction of the organic compound with the hydroperoxide, to be separated off at the bottom. It is also conceivable to lower the temperature at the bottom by, for example, addition of preferably gaseous, low-boiling components, e.g. the organic compound, preferably propene.

Examples of such low-boiling components include hydrocarbons having from 1 to 4 carbon atoms, for example methane, ethane, propane, butane, ethene or butenes. It is likewise possible to use, for example, nitrogen or argon.

Of course, it is also possible in the process of the present invention to react a plurality of organic compounds with the hydroperoxide. Likewise, it is conceivable for a plurality of hydroperoxides to be used for the reaction.

If a plurality of organic compounds and/or a plurality of hydroperoxides are reacted with one another in the respective steps, it is possible for various products resulting from the reactions to be present in the mixtures. If these are again separated off by distillation in the respective separation steps, it may be necessary to provide a plurality of distillation columns for the separation. Likewise, the removal of a plurality of hydroperoxides from the mixture by distillation may make a plurality of distillation columns necessary.

The reaction of the organic compound with the hydroperoxide in step (i) takes place in a reactor $R_I$ which is suitable for this purpose. Starting materials used for the reaction are the organic compound to be reacted, the hydroperoxide and, if necessary, one or more solvents which are appropriate and/or necessary in the reaction.

Thus, at least the streams $E_I^1$ and $E_I^2$ flow into the reactor $R_I$ in the process of the present invention. If desired, a further stream $E_I^3$, for example, can flow into the reactor $R_I$. Here, $E_I^1$ is the stream comprising the compound to be reacted, possibly dissolved in one or more solvents, $E_I^2$ is the stream comprising the hydroperoxide, possibly dissolved in one or more solvents, and $E_I^3$ is the stream comprising one or more solvents.

The individual streams $E_I^i$ are preferably combined to form one stream $E_I$ upstream of the inlet into the reactor $R_I$ in the process of the present invention. It is in principle likewise possible to introduce the individual streams individually into the reactor $R_I$. Furthermore, it is also possible for the individual streams to be combined in appropriate combinations before being introduced into the reactor $R_I$. For example, $E_I^1$ and $E_I^3$ could be combined upstream of the inlet into the reactor $R_I$ and be introduced into the reactor $R_I$ into which the stream $E_I^2$ additionally flows as a separate stream.

In the process of the present invention, a stream $E_I$ consisting of the combination of the streams $E_I^1$, $E_I^2$ and $E_I^3$ is preferably introduced into the reactor $R_I$. Here, preference is given to a stream in which the concentrations of the individual components of the stream are selected so that the stream is liquid and consists of a single phase.

The hydroperoxide concentrations in $E_I$ are preferably in the range from 0.01 to 10% by weight, particularly preferably in the range from 0.1 to 9% by weight, more particularly preferably in the range from 1 to 8% by weight and in particular in the range from 5 to 7% by weight.

The concentration of the organic compound to be reacted is, for example, selected so that the molar ratio of the organic compound to hydroperoxide is in the range from 0.7 to 3.0, preferably in the range from 0.8 to 2.7, more particularly preferably in the range from 0.9 to 2.3 and in particular in the range from 1.0 to 2.0.

Depending on the temperature selected for the reaction of the organic compound with the hydroperoxide in the reactor $R_I$, it may be useful in the process of the present invention to preheat the stream or streams prior to entry into the reactor $R_I$.

The reaction conditions in the reactor $R_I$ in the process of the present invention are selected so that the hydroperoxide conversion is generally in the range from 70 to 95%, preferably in the range from 80 to 94.5% and particularly preferably in the range from 85 to 94%.

Furthermore, pressure $p_I$, temperature $T_I$ and residence time $\Delta t_I$ of the reaction mixture in the reactor $R_I$ are preferably selected so that the mixture $M_I$ resulting from the reaction is liquid and consists of a single phase.

Here, pressures $p_I$ which are generally in the range from autogenous pressure to 100 bar, preferably in the range from autogenous pressure to 40 bar and particularly preferably in the range from autogenous pressure to 30 bar, are selected.

The temperatures $T_I$ are generally in the range from 0 to 120° C., preferably in the range from 10 to 100° C., more preferably in the range from 20 to 90° C. and particularly preferably in the range from 30 to 80° C.

After the reaction in the reactor $R_I$, the resulting mixture is passed as stream $M_I$ to the separation apparatus $A_I$. There, the hydroperoxide is separated from the mixture, as described above.

If, in the case of a separation by distillation, unreacted organic compound is also separated off, then the distillation is generally carried out so that at least 50%, preferably at least 60%, more preferably at least 70%, particularly preferably at least 80% and very particularly preferably at least 90%, of the reacted organic compound are separated from $M_I$.

The separation is preferably carried out so that a liquid mixture comprising the hydroperoxide is separated off. This mixture which has been separated off is hereinafter designated as $M_I^2$. It is also possible for the hydroperoxide-containing mixture which has been separated off to further comprise, in addition to the hydroperoxide, small amounts of, for example, unreacted organic compound and/or reacted organic compound. Likewise, the mixture $M_I^2$ comprising the hydroperoxide which has been separated off may further comprise necessary solvent which has been added via stream $E_I^3$ or solvent which may have been present in the streams $E_I^1$ and/or $E_I^2$.

If the unreacted organic compound is also separated off in the separation apparatus $A_I$, this separation, from which a liquid mixture or a liquid/gas mixture is preferably obtained, results in a stream which is hereinafter designated as $M_I^1$. In the process of the present invention, this may comprise, in addition to the reacted organic compound, the unreacted organic compound and/or small amounts of any necessary solvent which was added via the stream $E_I^3$ or solvent which may have been present in the streams $E_I^1$ and/or $E_I^1$.

If, as described above, the separation is carried out in a distillation unit and high-boiling components are separated off from $M_I$ at the bottom, then this separation results in a stream $M_I^3$. Such high-boiling components can be, for example, by-products of the reaction in the reactor $R_I$ which are present in the stream $M_I$.

After the steps (i) and (ii) have been carried out in the process of the present invention, the hydroperoxide which has been separated off is once again reacted with the organic compound in step (iii).

For example, it is possible to recirculate the stream $M_I^2$ comprising the hydroperoxide to the reactor $R_I$ and to react it there with the organic compound.

In the process of the present invention, various possible ways of recirculating $M_I^2$ to $R_I$ are conceivable.

Regardless of how the streams $E_I^1$ to $E_I^3$ are introduced into the reactor $R_I$, it is possible, for example, for $M_I^2$ to be introduced as a separate stream into $R_I$. Here, preheating of the stream $M_I^2$ is possible, as described above.

It is likewise possible, for example, to introduce $M_I^2$ into the stream $E_I^2$ before the resulting stream $E_I^2+M_I^2$ is introduced into $R_I$. It is likewise possible to mix $M_I^2$ into the stream $E_I$ resulting from the combination of $E_I^1$ to $E_I^3$ or into a suitable stream as described above resulting from a suitable combination of any two of the streams $E_I^1$ to $E_I^3$.

If a process variant in which $M_I^2$ is added to another stream upstream of the inlet into $R_I$ is chosen, then, for the purposes of the process of the present invention, the concentrations of the components of the corresponding streams are preferably set so that the resulting stream remains liquid and continues to consist of a single phase.

In a preferred embodiment of the process of the present invention, the stream $M_I^2$ is introduced into a second reactor $R_{II}$. The stream $M_I^2$ thus represents, in respect of the reactor $R_{II}$, in a manner analogous to the streams flowing into the reactor $R_I$, the stream $E_{II}^2$. Since renewed reaction of the hydroperoxide which has been separated off with the organic compound to be reacted takes place in the reactor $R_{II}$ in step (iii) of the process of the present invention, at least one further stream $E_{II}^1$ into the reactor $R_{II}$ is necessary. A stream $E_{II}^3$, for example, may also be necessary.

Here, in a manner analogous to the above-described streams $E_{II}^1$ to $E_I^3$, $E_{II}^1$ is the stream comprising the compound to be reacted, possibly dissolved in one or more solvents, $E_{II}^2$ is the stream comprising the hydroperoxide, possibly dissolved in one or more solvents, and $E_{II}^3$ is the stream comprising one or more solvents.

Likewise in a manner analogous to the above-described streams $E_I^i$, it is possible for the streams $E_{II}^i$ to be introduced into the reactor $R_{II}$ either individually or combined in suitable combinations. Preheating of the streams $E_{II}^i$ is likewise possible, as described above.

The stream $E_{II}^2$ is preferably combined with a stream $E_{II}^1+E_{II}^1$ or a stream $E_{II}^1+E_{II}^3$ and the resulting stream is introduced into $R_{II}$. The concentrations of the components of the streams $E_{II}^1$ and $E_{II}^3$ are preferably selected so that the stream $E_{II}$ flowing into the reactor $R_{II}$ is liquid and consists of a single phase.

The concentration of the organic compound to be reacted is selected so that the molar ratio of organic compound to hydroperoxide is preferably in the range from 0.7 to 10.0, more preferably in the range from 0.8 to 8.0, particularly preferably in the range from 0.9 to 6.0 and in particular in the range from 1.0 to 4.0.

As in the reactor $R_I$, the reaction in the reactor $R_{II}$ is carried out at a pressure $p_{II}$, a temperature $T_{II}$ and a residence time $\Delta t_{II}$ of the reaction mixture such that hydroperoxide conversions which are generally in the range of $\geq 90\%$, preferably in the range of $\geq 92\%$, more preferably in the range of $\geq 95\%$ and particularly preferably in the range from 95 to 99.5%, are achieved.

Pressures $p_{II}$ which are selected are generally in the range from autogenous pressure to 100 bar, preferably in the range from autogenous pressure to 40 bar and particularly preferably in the range from autogenous pressure to 30 bar.

The temperatures $T_{II}$ are generally in the range from 0 to 120° C., preferably in the range from 10 to 100° C., more preferably in the range from 20 to 90° C. and particularly preferably in the range from 30 to 80° C.

It is of course also possible in the process of the present invention for the mixture $M_{II}$ resulting from the reaction in the reactor $R_{II}$ to be taken from the reactor $R_{II}$ and, as described above, to be fed to a separation apparatus $A_{II}$ or even the separation apparatus $A_I$ and, if desired, for a third reaction to be carried out subsequently.

However, two reactors $R_I$ and $R_{II}$ and one separation apparatus $A_I$ are used in a preferred embodiment of the process of the present invention. The present invention accordingly provides a process in which the reactions in steps (i) and (iii) are carried out in two separate reactors.

As reactors, it is of course possible to use all conceivable reactors which are best suited for the respective reactions. In the process of the present invention, a reactor is not restricted to a single vessel. Rather, it is also possible to use a cascade of stirred vessels as, for example, reactor $R_I$ or, for example, reactor $R_{II}$.

Preference is given to using fixed-bed reactors as reactors in the process of the present invention. The present invention accordingly provides a process as described above in which fixed-bed reactors are used as reactors for the reactions. More preferably, fixed-bed tube reactors are used as fixed-bed reactors.

In particular, an isothermal fixed-bed reactor is used as reactor $R_I$ in the process of the present invention and an adiabatic fixed-bed reactor is used as reactor $R_{II}$.

The present invention therefore also provides an apparatus comprising an isothermal fixed-bed reactor (I), a separation apparatus (II) and an adiabatic fixed-bed reactor (III).

The present invention likewise provides for the use of this apparatus for the reaction of an organic compound with a hydroperoxide.

Furthermore, the present invention provides for this use in which the steps (i) to (iii) below:

(i) reaction of the hydroperoxide with the organic compound to give a mixture comprising the reacted organic compound and unreacted hydroperoxide, (ii) separation of the unreacted hydroperoxide from the mixture resulting from step (i), (iii) reaction of the hydroperoxide separated off in step (ii) with the organic compound, are carried out for the reaction of the organic compound with the hydroperoxide.

As hydroperoxide, all hydroperoxides known from the prior art which are suitable for the reaction of the organic compound can be used in the process of the present invention.

Examples of such hydroperoxides are tert-butyl hydroperoxide and ethylbenzene hydroperoxide, which are mentioned in the abovementioned SRI Report 2E "Propylene Oxide". Here, the tert-butyl hydroperoxide is prepared from isobutane and oxygen. The ethylbenzene hydroperoxide is prepared from ethylbenzene and oxygen.

In the present process, preference is given to using hydrogen peroxide as hydroperoxide. The present invention therefore also provides a process as described above in which the hydroperoxide used is hydrogen peroxide. Here, preference is given to using an aqueous hydrogen peroxide solution.

To prepare hydrogen peroxide, use can be made of, for example, the anthraquinone process by which virtually the entire world production of hydrogen peroxide is produced. This process is based on the catalytic hydrogenation of an anthraquinone compound to form the corresponding anthrahydroquinone compound, subsequent reaction of this with oxygen to form hydrogen peroxide and subsequent separation of the hydrogen peroxide formed by extraction. The catalysis cycle is closed by renewed hydrogenation of the anthraquinone compound which is obtained back.

An overview of the anthraquinone process is given in "Ullmann's Encyclopedia of Industrial Chemistry", 5th edition, volume 13, pages 447 to 456.

It is likewise conceivable to obtain hydrogen peroxide by anodic oxidation of sulfuric acid to convert it into peroxodisulfuric acid with simultaneous evolution of hydrogen at the cathode. Hydrolysis of the peroxodisulfuric acid then leads via peroxomonosulfuric acid to hydrogen peroxide and sulfuric acid, which is thus recovered. It is of course also possible to prepare hydrogen peroxide from the elements.

In the individual reactors, it is conceivable, in the case of an appropriate choice of the organic compound, to employ a reaction procedure in which the reaction of the organic compound with the hydroperoxide occurs under the indicated pressure and temperature conditions without addition of catalysts.

However, preference is given to a procedure in which one or more suitable catalysts are added to make the reaction more efficient; preference is in turn given to using heterogeneous catalysts. The present invention accordingly provides a process as described above in which the organic compound is brought into contact with a heterogeneous catalyst during the reaction.

It is in principle possible to use all heterogeneous catalysts which are suitable for the respective reaction. Preference is given to using catalysts which comprise a porous oxidic material such as a zeolite. Particular preference is given to using catalysts which comprise a titanium-, vanadium-, chromium-, niobium- or zirconium-containing zeolite as porous oxidic material.

Specific examples of suitable zeolites are titanium-, vanadium-, chromium-, niobium- and zirconium-containing zeolites having a pentasil zeolite structure, in particular the types assigned X-ray-crystallographically to the BEA, MOR, TON, MTW, FER, MFI, MEL, CHA, ERI, RHO, GIS, BOG, NON, EMT, HEU, KFI, FAU, DDR, MTT, RUT, RTH, LTL, MAZ, GME, NES, OFF, SGT, EUO, MFS, MWW or mixed MFI/MEL structures and also ITQ-4. It is also possible to use titanium-containing zeolites having the UTD-1, CIT-1 or CIT-5 structure in the process of the present invention. Further titanium-containing zeolites which might be mentioned are those having the ZSM-48 or ZSM-12 structure. Particular preference is given to using Ti zeolites having an MFI, MEL or mixed MFI/MEL structure in the process of the present invention. Further preference is given, specifically, to the, Ti-containing zeolite catalysts which are generally designated as "TS-1", "TS-2" and "TS-3", and also Ti zeolites having a skeletal structure isomorphous with β-zeolite.

Very particular preference is given to using a heterogeneous catalyst comprising the titanium-containing silicalite TS-1 in the process of the present invention.

It is possible to use the porous oxidic material itself as catalyst in the process of the present invention. However, it is of course also possible to use a shaped body comprising the porous oxidic material as catalyst. To produce the shaped body from the porous oxidic material, it is possible to use all methods of the prior art.

Before, during or after the one or more shaping steps in these methods, noble metals in the form of suitable noble metal components, for example in the form of water-soluble salts, can be applied to the catalyst material. This method is preferably employed to produce oxidation catalysts based on titanium silicates or vanadium silicates having a zeolite structure, making it possible to obtain catalysts which contain from 0.01 to 30% by weight of one or more noble metals selected from the group consisting of ruthenium, rhodium, palladium, osmium, iridium, platinum, rhenium, gold and silver. Such catalysts are described, for example, in DE-A 196 23 609.6, which, together with the catalysts described therein, is hereby fully incorporated by reference into the present application.

Of course, the shaped bodies can undergo a finishing treatment. All methods of comminution are conceivable, for example crushing or breaking the shaped bodies, likewise further chemical treatments, for example as described above.

When using a shaped body or a plurality thereof as catalyst, this can, in the process of the present invention, be regenerated after deactivation by means of a process in which regeneration is carried out by targeted burning-off of the deposits responsible for deactivation. This is preferably carried out in an inert gas atmosphere containing precisely defined amounts of oxygen-donating substances. This regeneration process is described in DE-A 197 23 949.8, which is in this respect fully incorporated by reference into the present application.

Among the reactions which are possible in the process of the present invention, the following may be mentioned by way of example:

the epoxidation of olefins, e.g. the preparation of propene oxide from propene and $H_2O_2$ or from propene and mixtures which provide $H_2O_2$ in situ; hydroxylations such as the hydroxylation of monocyclic, bicyclic or polycyclic aromatics to give monosubstituted, disubstituted or higher-substituted hydroxyaromatics, for example the reaction of phenol and $H_2O_2$, or of phenol and mixtures which provide $H_2O_2$ in situ, to form hydroquinone;

oxime formation from ketones in the presence of $H_2O_2$, or mixtures which provide $H_2O_2$ in situ, and ammonia (ammonoximation), for example the preparation of cyclohexanone oxime from cyclohexanone;

the Baeyer-Villiger oxidation.

In the process of the present invention, preference is given to reacting organic compounds which have at least one C—C double bond. The present invention accordingly provides a process as described above in which the organic compound has at least one C—C double bond.

Examples of such organic compounds having at least one C—C double bond are the following alkenes:

ethene, propene, 1-butene, 2-butene, isobutene, butadiene, pentene, piperylene, hexenes, hexadienes, heptenes, octenes, diisobutene, trimethylpentene, nonenes, dodecene, tridecene, tetradecene to eicosene, tripropene and tetrapropene, polybutadienes, polyisobutenes, isoprenes, terpenes, geraniol, linalool, linalyl acetate, methylenecyclopropane, cyclopentene, cyclohexene, norbornene, cycloheptene, vinylcyclohexane, vinyloxiran, vinylcyclohexene, styrene, cyclooctene, cyclooctadiene, vinylnorbornene, indene, tetrahydroindene, methylstyrene, dicyclopentadiene, dinvinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

The process of the present invention is preferably carried out using alkenes having from 2 to 8 carbon atoms. Particular preference is given to reacting ethene, propene and butene. Very particular preference is given to reacting propene.

A further advantage of the process of the present invention, apart from the fact that a smaller excess of organic compound to be reacted over hydroperoxide can be achieved, is that separating off hydroperoxide and reacting it again with the organic compound enables a higher total conversion of the hydroperoxide to be achieved. At the same time, further reactions of the product are reduced.

FIG. 1 shows a preferred embodiment of the apparatus. In this figure, $E_I$ is a stream comprising, for example, liquid propene, aqueous hydrogen peroxide solution and methanol, $R_I$ is an isothermal fixed-bed tube reactor, $M_I$ is a stream resulting from the reaction in reactor $R_I$, $A_I$ is a distillation column for taking off material at the top, via a side offtake and at the bottom, $M_I^1$ is a stream which is taken off at the top and comprises predominantly propene, propene oxide and methanol, $M_I^2$ is a stream which is taken off via a side offtake, comprises predominantly methanol and aqueous hydrogen peroxide solution and is passed to the reactor $R_{II}$, $M_I^3$ is a stream which is taken off at the bottom and comprises high-boiling by-products, for example methoxypropanols and propanetriol, from the reaction in reactor $R_I$, $M_I^4$ is an optional stream introduced into the distillation unit $A_I$ to keep the bottom temperature low, for example gaseous propene, $R_{II}$ is an adiabatic fixed-bed tube reactor, $E_{II}$ is a stream which comprises liquid propene and methanol and is introduced into the reactor $R_{II}$, $M_{II}$ is a stream from reactor $R_{II}$ comprising propene, propene oxide and methanol.

Figure 2:
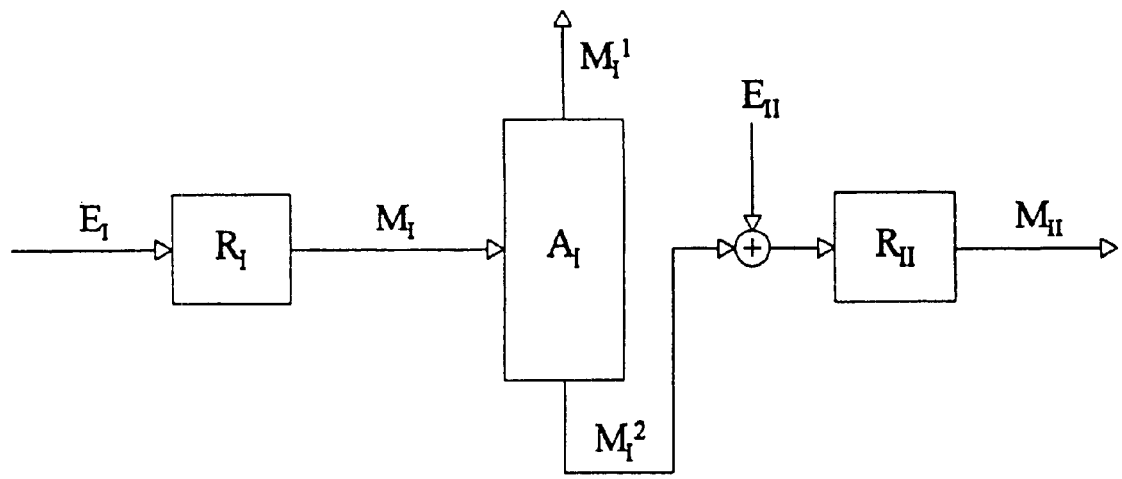

FIG. 2 shows a further preferred embodiment of the apparatus. In this figure, $E_I$ is a stream comprising, for example, liquid propene, aqueous hydrogen peroxide solution and methanol, $R_I$ is an isothermal fixed-bed tube reactor, $M_I$ is a stream resulting from the reaction in reactor $R_I$, $A_I$ is a distillation column from which material can be taken off at the top and at the bottom, $M_I^1$ is a stream which is taken off at the top and comprises predominantly propene, propene oxide and methanol, $M_I^2$ is a stream which is taken off at the bottom, comprises predominantly hydrogen peroxide, water, methanol and high-boiling by-products and is passed to the reactor $R_{II}$, $R_{II}$ is an adiabatic fixed-bed tube reactor, $E_{II}$ is a stream which comprises liquid propene and methanol and is introduced into the reactor $R_{II}$, $M_{II}$ is a stream from reactor $R_{II}$ comprising propene, propene oxide and methanol.

EXAMPLES

Example 1

Two-stage Procedure with Intermediate Separation

Flows of 10.5 g/h of hydrogen peroxide (about 40% strength by weight), 58 g/h of methanol and 10 g/h of propene are passed through a first tube reactor which has a reaction volume of about 50 ml and is charged with 23.1 g of TS-1 extrudates at a reaction temperature of 40° C. and a reaction pressure of 20 bar.

To analyze the output from the tube reactor, the reaction mixture was depressurized into a Sambay vaporizer against atmospheric pressure. The low boilers which were separated off were analyzed on-line in a gas chromatograph. The liquid reaction product was collected, weighed and likewise analyzed by gas chromatography.

The hydrogen peroxide yield achieved was 85%. The propene oxide selectivity based on hydrogen peroxide was 95%.

The output from the first reactor, which comprised methanol, water, propene oxide, by-products, unreacted propene and hydrogen peroxide, was depressurized into a column. The column was operated at atmospheric pressure and had about 15 theoretical plates.

At a bottom temperature of about 69° C., the propene oxide was separated off from the mixture to a level of <1% by weight.

The lower-boiling propene and some methanol together with propene oxide went over at the top. The runback necessary for the separation in the column was condensed at 50° C. in a partial condenser at the top. The top product was taken off in gaseous form and passed to work-up.

The bottom product was fed to a second tube reactor.

The bottom product from the intermediate separation and a propene stream of about 9 g/h were passed through a second tube reactor which had a reaction volume of about 50 ml and was charged with 28 g of TS-1 extrudates at a reaction temperature of 40° C. and a reaction pressure of 20 bar. After leaving the reactor, the reaction mixture was depressurized into a Sambay vaporizer against atmospheric pressure. The low boilers which were separated off were analyzed on-line in a gas chromatograph. The liquid reaction product was collected, weighed and likewise analyzed by gas chromatography.

The hydrogen peroxide conversion achieved was 96%. The propene oxide selectivity based on hydrogen peroxide was 96%.

The overall hydrogen peroxide conversion was 99.4% and the overall propene oxide selectivity was 95–96%. This gave a propene oxide yield based on hydrogen peroxide of 94–95%.

Example 2

Single-stage Procedure without Intermediate Separation

Flows of 8.3 g/h of hydrogen peroxide (about 40% strength by weight), 49 g/h of methanol and 7.8 g/h of propene were passed through a tube reactor which had a reaction volume of about 50 ml and was charged with 20 g of TS-1 extrudates at a reaction temperature of 40° C. and a reaction pressure of 20 bar.

After leaving the reactor, the reaction mixture was depressurized into a Sambay vaporizer against atmospheric pressure. The low boilers which were separated off were analyzed on-line in a gas chromatograph. The liquid reaction product was collected, weighed and likewise analyzed by gas chromatography.

The hydrogen peroxide conversion achieved was 98.4%. The propene oxide selectivity based on hydrogen peroxide was 80.3%. The propene oxide yield based on hydrogen peroxide was 79%.

What is claimed is:

1. A process of reacting an organic compound with a hydroperoxide, which comprises at least the steps (i) to (iii):
   (i) reacting a hydroperoxide with an organic compound to give a mixture comprising the reacted organic compound and unreacted hydroperoxide,
   (ii) separating the unreacted hydroperoxide from the mixture resulting from step (i),
   (iii) reacting the hydroperoxide separated in step (ii) with the organic compound,
   wherein said hydroperoxide is hydrogen peroxide, the organic compound is brought into contact with a heterogeneous catalyst during the reaction and the reactions in steps (i) and (iii) are conducted in two separate fixed-bed reactors.

2. A process as claimed in claim 1, wherein the heterogeneous catalyst comprises a titanium-containing silicalite.

3. A process as claimed in claim 1, wherein the organic compound has at least one C—C double bond.

4. An apparatus comprising an isothermal fixed-bed reactor (I), a separation apparatus (II) and an adiabatic fixed-bed reactor (III).

5. A method, comprising:
   reacting an organic compound with a hydroperoxide in the apparatus of claim 4.

6. The method as claimed in claim 5, wherein the steps (i) to (iii) of:
   (i) reacting a hydroperoxide with an organic compound to give a mixture comprising the reacted organic compound and unreacted hydroperoxide,
   (ii) separating the unreacted hydroperoxide from the mixture resulting from step (i),
   (iii) reacting the hydroperoxide separated in step (ii) with the organic compound, are conducted for the reaction of the organic compound with the hydroperoxide.

7. The method as claimed in claim 6, wherein the reaction in step (i) is carried out in an isothermal fixed-bed reactor (I), the separation in step (ii) is carried out by means of a separation apparatus (II) and the reaction in step (iii) is carried out in an adiabatic fixed-bed reactor (III).

8. The process according to claim 1, wherein the molar ratio of organic compound to hydroperoxide in the reaction ranges from 0.7 to 3.0.

9. The process according to claim 8, wherein the molar ratio of organic compound to hydroperoxide in the reaction ranges from 0.8 to 2.7.

10. The process according to claim 1, wherein the hydroperoxide conversion in step (i) ranges from 70 to 95%.

11. The process according to claim 10, wherein the hydroperoxide conversion in step (i) ranges from 80 to 94.5%.

12. The process according to claim 1, wherein the autogenous pressure in the reaction step ranges up to 100 bar.

13. The process according to claim 12, wherein the autogenous pressure in the reaction step ranges up to 40 bar.

14. The process according to claim 1, wherein the temperature of the reaction ranges from 0 to 120° C.

15. The process according to claim 14, wherein the temperature of the reaction ranges from 10 to 100° C.

* * * * *